United States Patent [19]
Kesson

[11] Patent Number: 4,550,590
[45] Date of Patent: Nov. 5, 1985

[54] METHOD OF AND APPARATUS FOR MONITORING CONCENTRATION OF GAS IN A LIQUID

[75] Inventor: James Kesson, Edinburgh, Great Britain

[73] Assignee: Scottish & Newcastle Breweries plc, Edinburgh, United Kingdom

[21] Appl. No.: 524,190

[22] Filed: Aug. 18, 1983

Related U.S. Application Data

[63] Continuation-in-part of Ser. No. 275,964, Jun. 22, 1981, Pat. No. 4,461,165.

[30] Foreign Application Priority Data

Aug. 24, 1982 [GB] United Kingdom ............... 8224218

[51] Int. Cl.[4] ............................................. G01N 7/10
[52] U.S. Cl. ..................................... 73/19; 73/61 R
[58] Field of Search ...................... 73/19, 61 R, 64.3

[56] References Cited
U.S. PATENT DOCUMENTS 3,673,853  7/1972  Griswold et al. ................... 73/19
3,681,026  8/1972  Holden ............................. 73/19 X
3,731,523  5/1973  Vissers et al. ....................... 73/19
3,866,460  2/1975  Pearce, Jr. ......................... 73/19
3,871,228  3/1975  Weiss ............................... 73/19

FOREIGN PATENT DOCUMENTS 1494441  12/1977  United Kingdom ................. 73/19

*Primary Examiner*—Stewart J. Levy
*Assistant Examiner*—Joseph W. Roskos
*Attorney, Agent, or Firm*—Mason, Fenwick & Lawrence

[57] ABSTRACT

There is described a method of and apparatus for monitoring the concentration of gas in a liquid. The apparatus includes a semi-permeable diaphragm across the face of which the liquid flows. Gas contained in the liquid permeates through the diaphragm into a chamber and the pressure within the chamber is measured. This pressure is representative of the concentration of gas in the liquid and permits control of the quantity of gas injected. In particular there is described a method and apparatus for monitoring the concentration of two different gases which may be dissolved in a flowing liquid.

11 Claims, 4 Drawing Figures

METHOD OF AND APPARATUS FOR MONITORING CONCENTRATION OF GAS IN A LIQUID

CROSS-REFERENCE TO RELATED APPLICATION

This application is a continuation-in-part of Ser. No. 275,964 filed on June 22, 1981 now U.S. Pat. No. 4,461,165.

Background of the Invention

This invention relates to a method of and to apparatus for monitoring the concentration of gas in a liquid.

The invention has particular application in the measuring and control of the content of dissolved gases such as carbon dioxide and oxygen in beer and lager. The $CO_2$ content in beer or lager is important in that the quality of the beer or lager is determined to some extent by the $CO_2$ content which varies according to the eventual packaging of the beer. For example, canned and bottled beer require a higher $CO_2$ content than kegged beer destined for draught.

Also, the detrimental effect of dissolved oxygen on the shelf life of canned and bottled beers, is one of the current problems encountered in the Brewing Industry.

The oxygen content in beer is generally at its lowest immediately post fermentation - levels at this stage are generally around 500 parts per billion. This usually arises during processing due to normal procedures, such as reinjection of runnings etc, addition of filter powder mixed with town liquor and storage in tanks top pressurised with air, and rises to levels which are fairly tolerable depending upon whether it is destined for long or short term packaging. It may also, however, rise dramatically to totally unacceptable levels due to plant failures, such as leaks at pump suctions which can draw in vast quantities of air, or through failures in deaerated liquor plants which occur during the blending operations.

Systems are known for measuring the gas content in beer but involve the use of a gas analyser which evaluates the volume concentration of $CO_2$ and oxygen in a sample of the beer.

Such systems are to some extent impractical insofar as a delay necessarily exists from the time the sample is taken to the time the results of the analysis are known and suitable adjustment of the quantity of $CO_2$ injected or correction of an excessive oxygen fault is effected. Additionally, gas analysers are expensive pieces of equipment and it is not feasible to provide each production line in a large bottling plant with its own analyser, thus resulting in further delay before control can be carried out.

SUMMARY OF THE INVENTION

It is an object of the present invention to obviate or mitigate the drawbacks and inconveniences of hitherto proposed systems and to provide a relatively economic means whereby the concentration of oxygen in a beer may be monitored.

According to the present invention there is provided a method of monitoring the concentration of gas in a liquid comprising passing said liquid across a semi-permeable membrane in order that gases in the liquid may permeate through the membrane into a chamber, and measuring the pressure of the permeated gases, evacuating said chamber after a predetermined period, and again measuring the pressure of the permeated gas.

Preferably, said measured pressure is corrected for the temperature of the liquid.

Further according to the present invention there is provided apparatus for monitoring the concentration of gas in a liquid comprising a semi-permeable membrane fixed in a housing and arranged to have one side in contact with said liquid, means defining a chamber on the side of said membrane remote from the liquid, means for evacuating said chamber and means for determining the pressure in said chamber.

Preferably, the pressure of the permeated gas is used to generate a pressure representative signal which is passed to a control unit which in turn produces a control signal to control the quantity of gas injected into the liquid.

DESCRIPTION OF THE DRAWINGS

Embodiments of the present invention will now be described, by way of example, with reference to the accompanying drawings, in which.

DESCRIPTION OF THE PREFERRED EMBODIMENTS

Figure 1:
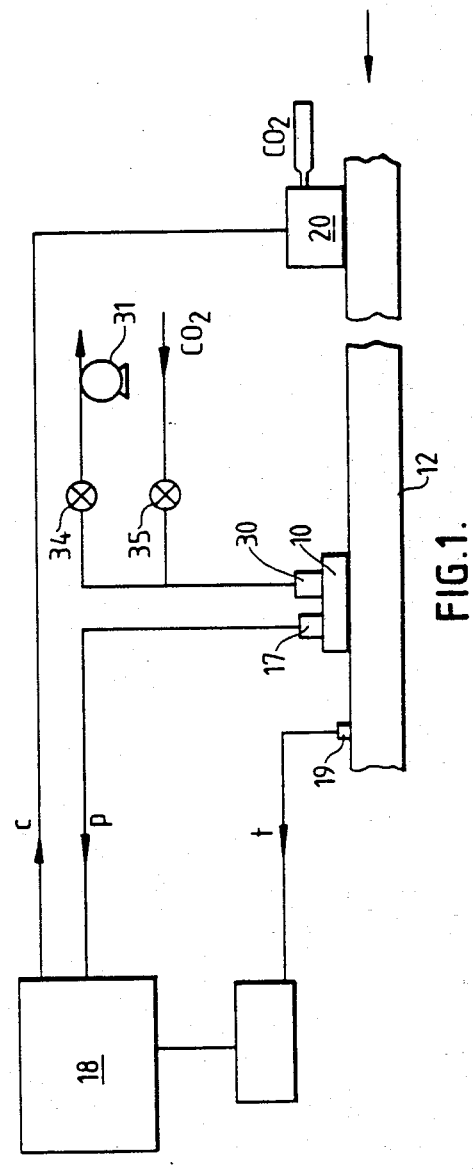
FIG. 1 shows schematically one embodiment of apparatus made in accordance with the present invention.
Figure 2:
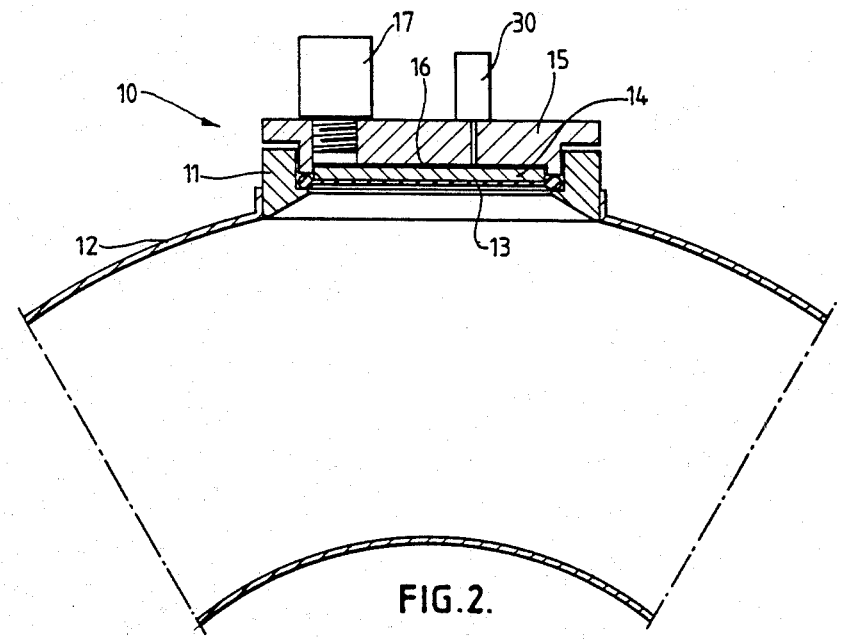
FIG. 2 is a sectional view of a basic embodiment of the pressure measuring device of the apparatus of FIG. 1 fitted to a pipe.
Figure 3:
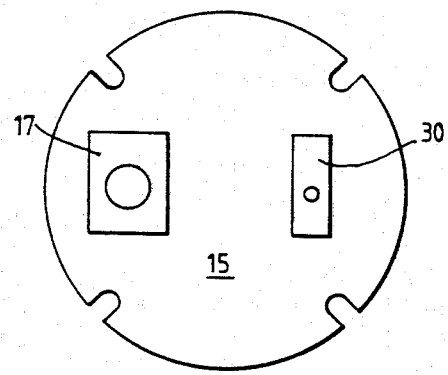
FIG. 3 is a top plan view of the top cover of the device of FIG. 2.

Referring to the drawings, apparatus for monitoring the gas concentration in a liquid comprises a pressure measuring device 10 in the form of a housing 11 fitted in a pipe 12 along which flows the liquid to be monitored. The housing 11 carries a semi-permeable membrane in the form of a silicone rubber diaphragm 13. The membrane material in this case is silicone rubber which has a permeation factor to $CO_2$ of approximately 28,000 (units:CC (STP)/$CM^2$/MM/SEC/CM), the material with the next highest factor being natural rubber with a factor of only 1,300 to 1,400. To prevent undue distention of the diaphragm 13 a gas-porous support disc 14 which can conveniently be formed of sintered steel is interposed between the diaphragm 13 and a top cover 15. The top cover 15 defines a chamber 16 into which gas contained in the liquid flowing along the pipe 12 diffuses. Thus, the pressure in the chamber is representative of the concentration of gas in the liquid. As the concentration of gas increases, the partial pressure of the gas in the liquid increases and more gas diffuses into the chamber 16 causing an increase in the pressure within the chamber. Similarly, as the concentration of gas decreases, the partial pressure decreases and gas diffuses out of the chamber 16 into the liquid causing a decrease in the pressure within the chamber.

The pressure in the chamber 16 is measured by means of a pressure transducer 17 which passes a pressure representative electrical signal (p) to a control and display unit 18. A temperature representative electrical signal (t) is derived from a temperature probe 19 and passed to the control unit 18. The pressure signal (p) is corrected for temperature and the value of gas concentration in the liquid is evaluated and displayed. Preferably, the gas concentration value is compared with a preset value and a control signal (c) is generated.

Should the concentration of gas fall outside the desired preset limits appropriate adjustment of the gas injection system 20 is carried out. Such adjustment is carried out automatically through an injection control unit 20 which receives the control signal (c) from the device control unit 18.

Thus, by virtue of a flow of gas through diaphragm 13 into and out of the chamber 16 equilibrium is maintained between the pressure of the gas in a chamber 16 and the partial pressure of the gas in the liquid, this partial pressure being representative of the concentration of gas in the liquid.

To avoid inaccurate readings, the chamber 16 is evacuated at start-up by means of a vacuum pump 31 through a solenoid operated vent valve 30 fitted to the top cover 15. Also, gas, for example CO2 from a supply may be introduced into the chamber 16 by appropriate operation of the valve 30 and of auxiliary solenoid valves 34 and 35.

Silicone rubber is highly selective, but is not exclusively permeable to CO2. The other two most common gases found in beer, and the only ones found in any quantity, are oxygen and nitrogen. It has been established that the relative rates of permeation between these gases is 30/5/1, i.e. CO2/oxygen/nitrogen. The relative quantities of CO2, oxygen and nitrogen in beer coupled with these permeation rates would at first sight render them into total insignificance. However, the pressure exerted by a dissolved gas in any liquid is inversely proportional to its solubility in that liquid. A saturated solution of air and water at atmospheric pressure exerts a pressure of 14.7 psi which occurs, depending upon temperature, at oxygen levels between 10,000 and 14,000 parts per billion, which means that even at the relatively low levels of oxygen found in beers a considerable error can be introduced into the CO2 measurement.

Due to the differential permeation rates between oxygen and CO2 of approximately 1 to 6, it is possible to maintain the accuracy of the CO2 reading by periodically re-initiating or refreshing the measuring cell, this operation now being executed in approximately 60 seconds causes little or no disruption to the plant and the injection rate is maintained at the level prior to the refresh period. Refresh periods are normally initiated at 15 minute intervals, this interval being selected because beer with around 1,500 PPB oxygen after 15 minutes would, depending upon the temperature, cause a positive error of 0.1 volumes to the CO2 reading. The effect of this in the receiving tank would be that the level of CO2 would be 0.05 volumes above the desired value setting of the instrument. For higher levels of dissolved oxygen or for greater accuracy, more frequent refreshes would be necessary.

The pressure in the measuring cell, immediately prior to the first refresh cycle, is the CO2 pressure plus the pressure of the oxygen, and immediately after is largely that of the CO2 because of the differential permeation rates. The difference, therefore, is a measure of the dissolved oxygen which can now be displayed as an actual reading in the chosen units and further CO2 readings may be displayed with far greater accuracy because of this knowledge. The permeation of nitrogen with its 1 to 30 rate differential to CO2 can safely be ignored, except possibly in the case of beers with nitrogen enrichment which have not been evaluated at the time of writing. If the oxygen levels have risen to the near saturation point, no finesse is required to detect the condition since the apparent CO2 level rises to an easily detected and improbable value. The instrument can therefore prevent a large amount of beer being canned after an undetected failure in for example a deaerated liquor plant supplying liquor to the blending point.

Figure 4:
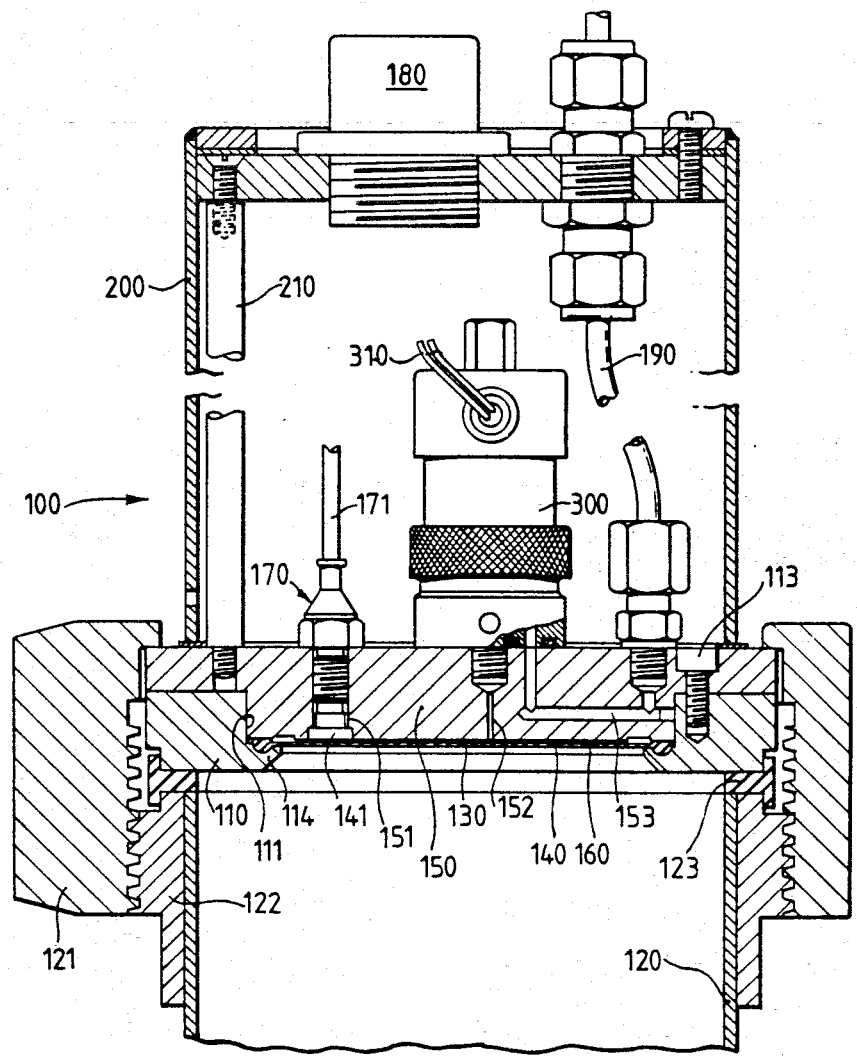
FIG. 4 is a sectional view, in elevation, of an improved embodiment of the pressure measuring device of the apparatus of FIG. 1.

Referring now to FIG. 4 of the drawings, there is illustrated an improved embodiment of apparatus made in accordance with the present invention.

In the drawings, a pressure measuring device 100 has a base 110 having a circular opening 111 in which there is received a main body 150. The main body 150 is held in the opening 111 by screws 113. The resultant cylindrical combination is illustrated fixed to a branch pipe 120 by means of a ring nut 121 which cooperates with a threaded portion 122 of the pipe 120. A suitable seal 123 is provided and the pipe 120 communicates with a main pipe along which flows the liquid to be monitored.

A semi-permeable membrane in the form of a silicone rubber diaphragm 130 is held between the peripheral edge of the lower face of the body 150 and a circular ridge 114 of the case 110.

A chamber 160 is thus defined between the lower face of the body and the upper face of the diaphragm 130. A wire mesh screen 140 within the chamber 160 is interposed between these two faces and serves to avoid any distortion of the diaphragm.

Thus, the membrane is supported in such a manner as to withstand high pressures and allow the permeated gas free access in the sealed chamber in order that the pressure measured there is truly representative of the equilibrium pressure. This is achieved by use of the fine stainless steel mesh backing the membrane which is self-sealing with an integral moulded 'O' ring. It is important that the volume in the sealed chamber is kept to an absolute practical minimum requiring a very high tolerance of maching and dictating also that a suitable type of pressure sensor, because of its extremely small 'dead' volume, is that of the Piezo-resistive type. The membrane carrier and cover are constructed of stainless steel and are designed to be fitted into a tee piece with a shortened leg, and the whole is retained by a ring nut. The leg of the tee must be short, not only for hygienic reasons but for response time, since the dissolved $CO_2$ in a standard tee will not necessarily be representative of the beer in the main flow.

The main body 150 is provided with a first through orifice 151 into which there is fitted a pressure transducer 170 which communicates with the chamber 160 via a sintered bronze insert 141. A pressure representative signal from the transducer 170 is passed to a control unit through suitable wiring 171 to a connector 180.

A second through orifice 152 serves to connect the chamber 160 with one port of a solenoid operated valve 300. The valve 300 is operated by means of wiring 310 connected to connector 180. The other port of the valve 300 connects with passageways 153 drilled in the body 150 which in turn connects with pipe 190. The pipe 190 connects with a vacuum pump and supply of gas, for example, CO2, whereby the chamber 160 may be evacuated, vented to atmosphere, or charged with gas, thereby to increase the accuracy of measurement of the device.

To protect the transducer 170, valve 300 and pipe 190, the device is provided with a hollow cylindrical cover 200 supported by pillars 210 and fixed on the body 150.

The device of FIG. 4 operates as follows.

As the liquid flows from the main pipe into branch pipe 120, gas contained in the liquid diffuses through the diaphragm 130 into and out of the chamber 160. As the concentration of the gas within the liquid changes, the partial pressure of the gas in the liquid changes proportionally. This change results in a pressure differential across the diaphragm 160 and gas flows into or out of the chamber until equilibrium is achieved. Thus, the pressure in the chamber, as detected by the transducer 170 is representative of the concentration of gas in the liquid.

Hitherto, the measurement on which the reading was produced invariably depended upon the rate of permeation and accordingly was a relative measurement. In the device of the present invention the rate of permeation affects only the response time and, because the pressure of the dissolved gases always approaches equilibrium, the instrument produces an absolute measurement of the pressure of the dissolved gases.

The signal from the transducer 170 can thus be used to control the quantity of the gas injected into the liquid and therefore a desired level of concentration can be achieved.

Accordingly, there has been described a method of and apparatus for monitoring the concentration of gas in a liquid. The apparatus provides on-line control of the quantity of gas in the liquid.

Thus, the pressure measured by the transducer is the equilibrium pressure of the gas dissolved in the liquid and the resistance thermometer measures the temperature, and these two parameters are interrogated by a micro-computer—which by reference to a table calculates the total dissoled gas in volumes/volume.

The solenoid valve 300 incorporated in the measuring head allows the sealed chamber to be connected to a vacuum exhauster unit. The main function of this unit is to refresh the cell on start-up and remove any air which is present and which would give erroneous readings. The computer also generates the basic control algorithms, proportional and integral, and produces a corrective analogue output which will modulate the CO2 injection rate to achieve the desired value as set upon the thumbwheels in the front panel.

Modifications and improvements may be incorporated without departing from the scope of the invention. For example, two measuring cells which will allow for the continuous monitoring of the oxygen as opposed to the periodic alarm may be provided. The instrument, although primarily developed for use in the Brewing Industry, has application also in the Soft Drinks Industry.

I claim:

1. A method of monitoring the concentration of gas in a liquid comprising the steps of:
   passing said liquid across a semi-permeable membrane in order that gases in the liquid may permeate through the membrane into a chamber;
   measuring the pressure in said chamber after a predetermined first period to obtain a first pressure reading, said first period being such as to allow permeation of a first gas and a second gas through said membrane until equilibrium conditions with respect to both gases is reached;
   evacuating said chamber;
   measuring the pressure in said chamber after a second, relatively shorter period to obtain a second pressure reading, said second period being sufficient to allow equilibrium conditions with respect only to said first gas to be reached; and
   deriving from said first and second pressure readings a reading indicative of the concentration of said second gas in said liquid.

2. A method as claimed in claim 1, wherein said pressure readings are corrected for the temperature of the liquid.

3. Apparatus for monitoring the concentration of gas in a liquid comprising:
   a semi-permeable membrane fixed in a housing and arranged to have one side in contact with said liquid;
   means defining a chamber on the side of said membrane remote from the liquid;
   means for evacuating said chamber; and
   means for determining the pressure in said chamber;
   wherein the pressure of the permeated gas is used to generate a pressure representative signal which is passed to a control unit which, in turn, produces a control signal to control the quantity of gas injected into the liquid, and wherein said housing includes an annular base having a circular opening, a main body overlying said circular openings and clampingly holding said semi-permeable membrane in position covering said circular opening, said chamber being defined by a surface of said main body and said semi-permeable membrane, a gas-porous support means overlying said semi-permeable membrane in said chamber, said means for determining the pressure in said chamber comprising a pressure transducer mounted in said main body and wherein said means for evacuating said chamber includes an orifice extending through said main body and communicating with a solenoid valve and a vacuum source connected to said solenoid valve.

4. The apparatus of claim 3 wherein said gas is carbon dioxide and said semi-permeable membrane is formed of silicone rubber.

5. The apparatus of claim 4 wherein said semi-permeable membrane has a permeation factor of 28,000 CC(STP)/CM$^2$/MM/SEC/CM.

6. The apparatus of claim 3 wherein said gas-porous support means is a wire mesh screen.

7. The apparatus of claim 6 wherein said gas is carbon dioxide and said semi-permeable membrane is formed of silicone rubber.

8. The apparatus of claim 7 wherein said semi-permeable membrane has a permeation factor of 28,000 CC(STP)/CM$^2$/MM/SEC/CM.

9. The apparatus of claim 7 wherein said pressure transducer is a piezo-resistive type.

10. The apparatus of claim 9 wherein said liquid is beer.

11. Apparatus for monitoring the concentration of gas in a liquid comprising:
    a semi-permeable membrane fixed in a housing and arranged to have one side in contact with said liquid;
    means defining a chamber on the side of said membrane remote from the liquid;
    means for evacuating said chamber and means for determining the pressure in said chamber;
    wherein said housing includes an annular base having a circular opening, a main body overlying said circular opening and clampingly holding said semi-permeable membrane in position covering said circular opening, said chamber being defined by a surface of said main body and said semi-permeable membrane, a gas-porous support means overlying said semi-permeable membrane in said chamber, said means for determining the pressure in said chamber comprises a pressure transducer mounted in said main body, and wherein said means for evacuating said chamber includes an orifice extending through said main body and communicating with a solenoid valve and a vacuum source connected to said solenoid valve.

* * * * *